United States Patent
Majeed et al.

(10) Patent No.: US 11,123,382 B2
(45) Date of Patent: Sep. 21, 2021

(54) **HAIR CARE COMPOSITIONS CONTAINING EXTRACELLULAR METABOLITE PREPARATION FROM *BACILLUS COAGULANS***

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US); Lakshmi Mundkur, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 184 days.

(21) Appl. No.: 15/995,454

(22) Filed: Jun. 1, 2018

(65) Prior Publication Data

US 2018/0344781 A1  Dec. 6, 2018

Related U.S. Application Data

(60) Provisional application No. 62/516,077, filed on Jun. 6, 2017.

(51) Int. Cl.
| | | |
|---|---|---|
| *A61K 35/742* | (2015.01) | |
| *A61K 9/00* | (2006.01) | |
| *A61P 17/08* | (2006.01) | |
| *A61P 17/14* | (2006.01) | |
| *A61Q 7/00* | (2006.01) | |
| *A61K 8/99* | (2017.01) | |
| *A61K 47/32* | (2006.01) | |
| *A61K 47/18* | (2017.01) | |
| *A61K 47/44* | (2017.01) | |

(52) U.S. Cl.
CPC .............. *A61K 35/742* (2013.01); *A61K 8/99* (2013.01); *A61K 9/0014* (2013.01); *A61K 47/183* (2013.01); *A61K 47/32* (2013.01); *A61K 47/44* (2013.01); *A61P 17/08* (2018.01); *A61P 17/14* (2018.01); *A61Q 7/00* (2013.01)

(58) Field of Classification Search
None
See application file for complete search history.

(56) References Cited

U.S. PATENT DOCUMENTS

| | | | | |
|---|---|---|---|---|
| 6,905,692 B2 * | 6/2005 | Farmer | ................ | A01N 63/00 |
| | | | | 424/260.1 |
| 8,197,865 B2 * | 6/2012 | Glynn | ................ | A61K 8/9794 |
| | | | | 424/727 |
| 8,492,127 B2 * | 7/2013 | Xu | ................ | C12P 7/56 |
| | | | | 435/139 |

FOREIGN PATENT DOCUMENTS

EP  1 097 700 A1 *  5/2001

OTHER PUBLICATIONS

Kim et al. Biol. Pharm Bull 1999,22(12), 1396-1399.*
Guidelines for the evaluation of probiotics in food, Joint FAO/WHO Working Group Report on Drafting Guidelines for the Evaluation of Probiotics in Food, London, Ontario, Canada, Apr. 30 and May 1, 2002.
Mannu et al. (2003) Comparison of the incidence of virulence determinants and antibiotic resistance between Enterococcus faecium strains of dairy, animal and clinical origin. International Journal of Food Microbiology 88:291-304.
Pinu et. al., (2017) Extracellular Microbial Metabolomics: The State of the Art; Metabolites, 7:43. doi:10.3390/metabo7030043.
Ruiz et al., (2014) Extracellular molecular effectors mediating probiotic attributes, FEMS Microbiol Lett 359:1-11.

* cited by examiner

*Primary Examiner* — Vera Afremova

(57) ABSTRACT

Disclosed are hair care compositions containing partially purified extracellular metabolite preparation from strains of *Bacillus coagulans*. Specifically, the uses of compositions containing extracellular metabolite preparation from a strain of *Bacillus coagulans* for increasing hair growth, inhibition of 5α-reductase and proliferation of follicle dermal papilla cells and in the management of androgenic alopecia, are disclosed.

3 Claims, 4 Drawing Sheets
(1 of 4 Drawing Sheet(s) Filed in Color)

HAIR CARE COMPOSITIONS CONTAINING EXTRACELLULAR METABOLITE PREPARATION FROM *BACILLUS COAGULANS*

CROSS-REFERENCE TO RELATED APPLICATIONS

This is a non-provisional application claiming priority from U.S. provisional application No. 62/516,077 filed on 6 Jun. 2017

BACKGROUND OF THE INVENTION

Field of the Invention

The invention in general relates to hair care compositions. More specifically the invention relates to hair care composition containing partially purified extracellular metabolite preparation from *Bacillus coagulans*.

Description of Prior Art

Hair is one of the fastest growing tissues of the human body. Hair follicles undergo repetitive regenerative cycles consisting of three stages: anagen (rapid growth, active stage), catagen (apoptosis-driven regression, physiological involution stage), and telogen (resting stage). Reduction in anagen stage can result in miniaturization of hair follicles and hair loss. Thus extending the anagen phase is an effective treatment for the prevention of hair loss.

Growth and proliferation of follicle papilla cells are important for increasing the number of hair follicles and thereby to promote hair growth. Dermal papilla cells accumulate below undifferentiated epidermis which is then stimulated to form the hair "peg". Interaction between the hair peg and the dermal papilla cells promotes differentiation into a mature hair follicle. During the anagen phase the dermal papilla cells secrete several growth factors, like insulin like growth factor (IGF-1), fibroblast growth factor (FGF-7) which stimulates the proliferation and elongation of hair shaft. Hence, the dermal papilla has to be present in good numbers to ensure sufficient hair growth. Certain clinical conditions like androgenic alopecia, seborrhoeic dermatitis (dandruff) etc reduce the number of dermal papilla and increase hair fall. TGF-$\beta$2 is specifically expressed in human dermal papilla cells. TGF-$\beta$ has been shown to exert unique multidirectional effect by inducing premature hair follicle regression in adult hair growth cycle and is required for hair folliculogenesis. The role of TGF-$\beta$ is well documented in the following references:

1. Foitzik K, Paus R, Doetschman T, et al. The TGF-$\beta$2 isoform is both a required and sufficient inducer of murine hair follicle morphogenesis. Dev Biol. 1999; 212:278-89
2. Hibino T, Nishiyama T. Role of TGF-$\beta$2 in the human hair cycle. J Dermatol Sci. 2004; 35: 9-18.
3. Jamora C, Lee P, Kocieniewski P, et al. A signaling pathway involving TGF-$\beta$2 and snail in hair follicle morphogenesis. PLoS Biol. 2004; 3: e11.
4. Keita Inoue, Noriyuki Aoi, Yuji Yamauchi, Takahiro Sato, Hirotaka Suga, Hitomi Eto, Harunosuke Kato, Yasuhiko Tabata, Kotaro Yoshimura. TGF-$\beta$2 is specifically expressed in human dermal papilla cells and modulates hair folliculogenesis J. Cell. Mol. Med. Vol 13, No 11-12, 2009 pp. 4643-4656

Vascular endothelial growth factor (VEGF) is essential for angiogenesis and vascular permeability and is responsible for maintaining proper vasculature around the hair follicle during the anagen growth phase. VEGF mRNA is strongly expressed in dermal papilla cells (DPC) in the anagen phase, but during the catagen and telogen phases. VEGF mRNA is less strongly expressed (Kozlowska et al., Expression of vascular endothelial growth factor (VEGF) in various compartments of the human hair follicle Arch Dermatol Res (1998) 290:661-668; Yano et al., Control of hair growth and follicle size by VEGF-mediated angiogenesis *J Clin Invest.* 2001; 107(4):409-417). Both VEGF and TGF-$\beta$2 promote the proliferation of dermal papilla cells and thereby increase hair growth.

The dermal papilla also produces an enzyme called 5$\alpha$-reductase (3-oxo-5$\alpha$-steroid-delta 4-dehydrogenase), a NADPH-dependent enzyme, which converts Testosterone to dihydrotestosterone (DHT). Overproduction of 5$\alpha$-reductase increases the conversion of testosterone to DHT in hair follicles, thereby disrupting the natural hair cycle leading to hair fall and development of androgenic alopecia.

Natural 5$\alpha$-reductase inhibitors like mushrooms, green tea etc. slow down the production of DHT and prevent hair loss. The use of probiotic in hair care in now garnering attention owing to the fact that probiotics can alter the microbiome of the skin responsible for hair loss. U.S. Pat. No. 7,374,750, discloses a composition containing a probiotic organism for hair care. The beneficial effects of probiotics for hair growth and increasing follicle dermal papilla is also well documented by Levkovich et al. (2013); Probiotic Bacteria Induce a 'Glow of Health", PLoS One. 2013; 8(1): e53867. Probiotics and their extracellular products are also reported to exhibit excellent anti-fungal activity, making them a valuable addition individually or as an adjuvant in anti-dandruff compositions.

It is well known in the scientific art that biological effects of probiotics or products thereof are strain specific and cannot be generalised among genera, species and strains (Probiotics: In Depth/NCCIH, U.S. Department of Health and Human Services, National Institutes of Health). Hence, there exists a need to find a superior probiotic strain and its extracellular product which promotes the growth of dermal papilla cells and prevents hair loss by inhibiting the 5$\alpha$-reductase. Also, the beneficial effects of extracellular product obtained from probiotics on hair growth remain to be validated. The present invention solves the above problem by disclosing the beneficial effect of partially purified extracellular metabolite preparation of *Bacillus coagulans* on dermal papilla proliferation.

It is the principle objective of the invention to disclose a composition containing the partially purified extracellular metabolite preparation of *Bacillus coagulans* to increase hair growth.

It is another objective of the invention to disclose a composition containing the partially purified extracellular metabolite preparation of *Bacillus coagulans* to inhibit the activity of 5$\alpha$-reductase.

It is yet another objective of the invention to disclose a composition containing the partially purified extracellular metabolite preparation of *Bacillus coagulans* for use in the therapeutic management of androgenic alopecia.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh—160036, India.

SUMMARY OF THE INVENTION

The present invention discloses a hair care composition containing the partially purified extracellular metabolite preparation isolated from a strain of *Bacillus coagulans*. More specifically, the invention discloses the use of a composition containing the extracellular metabolite isolated from a strain of *Bacillus coagulans* for the enhancing hair growth by increasing the proliferation follicle dermal papilla cells and inhibition of 5α-reductase.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DESCRIPTION OF THE MOST PREFERRED EMBODIMENTS

Figure 1A:
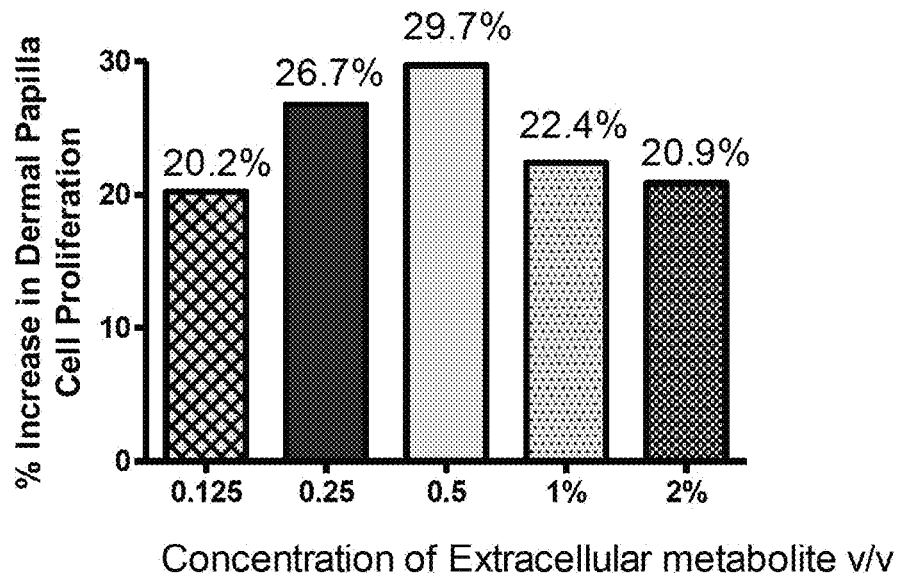
FIG. 1*a* is the graphical representation of the percentage increase in dermal papilla cell proliferation compared to control by partially purified extracellular metabolite preparation from *Bacillus coagulans* MTCC 5856.

In a most preferred embodiment, the invention discloses a hair care composition containing the partially purified extracellular metabolite preparation from a strain of *Bacillus coagulans* formulated with pharmaceutically/cosmeceutically acceptable excipients, adjuvants, bases, diluents, carriers, conditioning agents and preservatives. In a related embodiment, the composition containing the partially purified extracellular metabolite preparation from a strain of *Bacillus coagulans* can be combined with and/or incorporated into formulations containing hair care ingredients. In another related embodiment, the hair care composition is administered topically in the form of creams, gels, lotions, shampoo, serum, oil, suspensions, emulsions, and compacts. In another embodiment, the strain of *Bacillus coagulans* is selected from the group consisting of *Bacillus coagulans* MTCC 5856, *Bacillus coagulans* ATCC 31284 and *Bacillus coagulans* ATCC 7050.

In another related embodiment, the invention relates to a method of increasing hair growth in mammals, said method comprising steps of administering effective concentration of partially purified extracellular metabolite preparation from a strain of *Bacillus coagulans* to said mammals, to bring about increase in hair growth. In a related embodiment, the increase in hair growth is brought about by a) increasing the expression of secretory factors and b) increasing the proliferation of follicle dermal papilla cells. In another related embodiment, the secretory factors are selected from the group consisting of vascular endothelial growth factor (VEGF) and transforming growth factors-β (TGF-β). In another related embodiment, the effective concentration of the partially purified extracellular metabolite preparation is 0.01% v/v to 2.0% v/v of the total composition. In another embodiment, the strain of *Bacillus coagulans* is selected from the group consisting of *Bacillus coagulans* MTCC 5856, *Bacillus coagulans* ATCC 31284 and *Bacillus coagulans* ATCC 7050

In another preferred embodiment, the invention relates to a method of inhibiting 5α-reductase activity, said method comprising step of bringing into contact said follicle dermal papilla cells with effective concentration of partially purified extracellular metabolite preparation from a strain of *Bacillus coagulans* to bring about 5α-reductase inhibition in follicle dermal papilla cells. In a related embodiment, the effective concentration of the partially purified extracellular metabolite preparation in the composition is 0.01% v/v to 2.0% v/v of the total composition. In another embodiment, the strain of *Bacillus coagulans* is selected from the group consisting of *Bacillus coagulans* MTCC 5856, *Bacillus coagulans* ATCC 31284 and *Bacillus coagulans* ATCC 7050.

In another preferred embodiment, the invention discloses a method for therapeutic management of androgenic alopecia in mammals, said method comprising steps administering an effective concentration of a composition containing partially purified extracellular metabolite preparation from a strain of *Bacillus coagulans* to mammals in need of such therapy. In a related embodiment, the composition is formulated with pharmaceutically/cosmeceutically acceptable excipients, adjuvants, bases, diluents, carriers, conditioning agents and preservatives and/or incorporated into formulations containing hair care ingredients and administered topically in the form of creams, gels, lotions, shampoo, serum, oil, suspensions, emulsions, and compacts. In a related embodiment, the effective concentration of the partially purified extracellular metabolite preparation in the composition is 0.01% v/v to 2.0% v/v of the total composition. In another embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another related embodiment, the mammal is preferably human.

In another preferred embodiment, the invention discloses a method for therapeutic management of seborrhoeic dermatitis in mammals, said method comprising steps administering an effective concentration of a composition containing partially purified extracellular metabolite preparation from a strain of *Bacillus coagulans*, along with standard anti-dandruff ingredients to mammals in need of such therapy. In a related embodiment, the composition is formulated with pharmaceutically/cosmeceutically acceptable excipients, adjuvants, bases, diluents, carriers, conditioning agents and preservatives and administered topically in the form of creams, gels, lotions, shampoo, serum, oil, suspensions, emulsions, and compacts. In another embodiment, the anti-dandruff ingredients are selected from the group consisting of, but not limited to, coleus oil, tea tree oil, clove oil, basil oil and extract, rosemary oil, neem extract, cedarwood oil, selenium sulphide, Zinc Pyrithione, Salicylic acid, Ketoconazole, Climbazole and Ciclopirox Olamine. In a related embodiment, the effective concentration of the partially purified extracellular metabolite preparation in the composition is 0.01% v/v to 2.0% v/v of the total composition. In another embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another related embodiment, the mammal is preferably human.

Specific illustrative examples enunciating the most preferred embodiments are included herein below

Example 1: Proliferation of Dermal Papilla

Isolation of Extracellular Metabolite

The extracellular metabolite from *Bacillus coagulans* MTCC 5856 was isolated as per the steps outlined in U.S. Pat. No. 9,596,861 which is herein incorporated by reference. The product is commercially available under the tradename LACTOSPORIN® (INCI: *Bacillus* ferment filtrate extract) from Sabinsa Corporation, USA.

Materials and Method

Cells: Dermal Papilla Cells (human HFDPC) were purchased from Promocell (Germany), and maintained as a monolayer culture in Fibroblast growth media (Promocell, Germany) at 37° C. in a humidified 5% $CO_2$ incubator. Dermal Papilla Cells were cultured in DMEM supplemented with 10% FBS. The confluent cultures were harvested by trypsinization and expanded during two more passages before they were used for the experiments. Medium and other culture components were renewed after 48-72 h. All cell cultures were maintained at 37° C. in 95% air and 5% $CO_2$ in a $CO_2$ incubator.

The Dermal Papilla Cells were used for the assay at a seeding density of 2000 cells per well of 24-well clear bottom microplate in DMEM and incubated at 37° C. in 95% air and 5% $CO_2$ in a $CO_2$ incubator for 24 hours. The cell monolayers were fixed with 50% (w/v) trichloroacetic acid for 1 hour at 4° C. and stained with 0.4% SRB for 30 min. The excess dye was removed by washing repeatedly with 1% (v/v) acetic acid. The protein-bound dye is dissolved in 10 mMTris base solution and the optical density (OD) was read at 492 nm using a microplate reader. Cell proliferation in the presence of the samples was calculated based on the increased optical density due to the viable cells, as percentage of proliferation compared to the controls in the absence of test samples.

Results

Figure 1B:
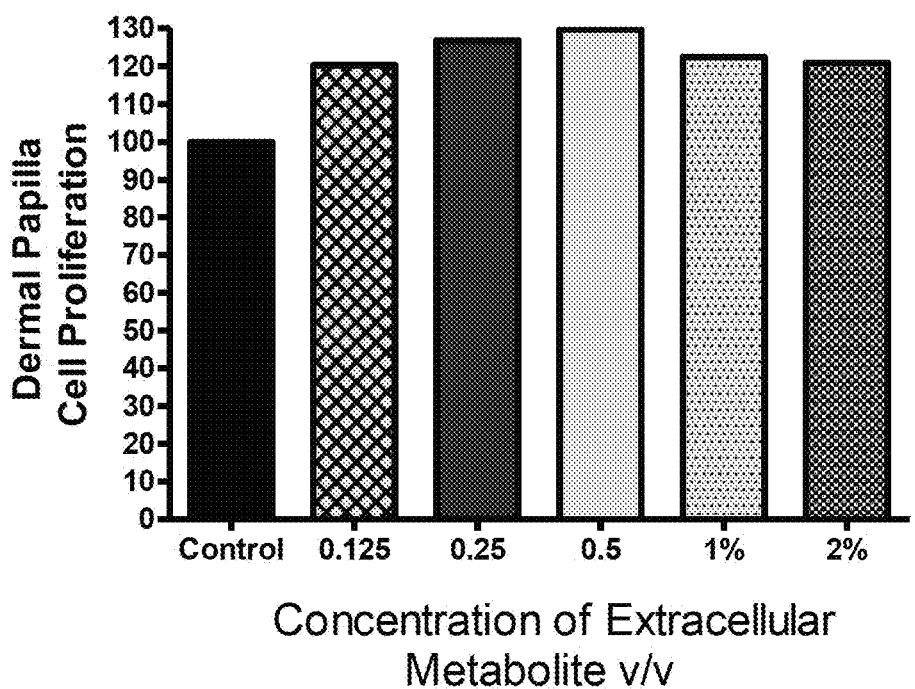
FIGS. 1*b* and 1*c* depict the dose dependent increase in the proliferation of dermal papilla cells in the presence of partially purified extracellular metabolite preparation from *Bacillus coagulans* MTCC 5856.
Figure 1C:
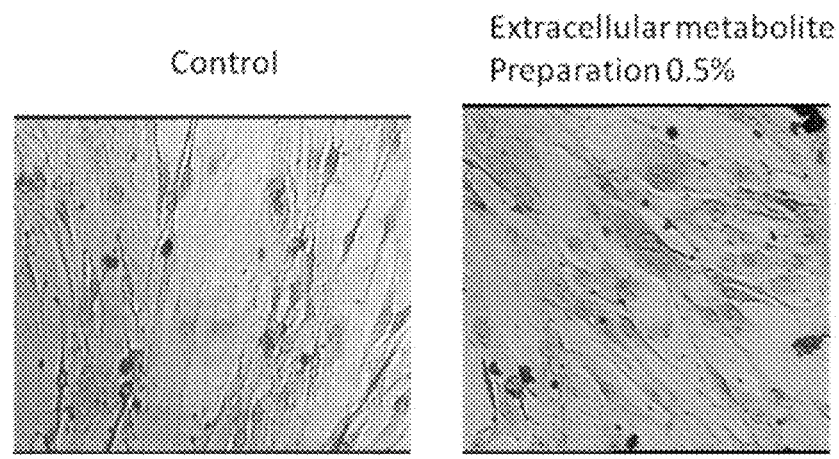

The results indicated that the extracellular metabolite preparation increased the proliferation of Dermal papilla cells (FIGS. 1a, 1b and 1c). It also stimulated the anagen phase of follicular cell growth indicating its potential as a hair care cosmetic.

Expression of Secretory Factors

Materials and Method

Cells: Dermal Papilla Cells (human HFDPC) were purchased from Promocell (Germany), and maintained as a monolayer culture in Fibroblast growth media (Promocell, Germany) at 37° C. in a humidified 5% $CO_2$ incubator. Dermal Papilla Cells were cultured in DMEM supplemented with 10% FBS. The confluent cultures were harvested by trypsinization and expanded during two more passages before they were used for the experiments. Medium and other culture components were renewed after 48-72 h. All cell cultures were maintained at 37° C. in 95% air and 5% $CO_2$ in a $CO_2$ incubator.

Figure 2:
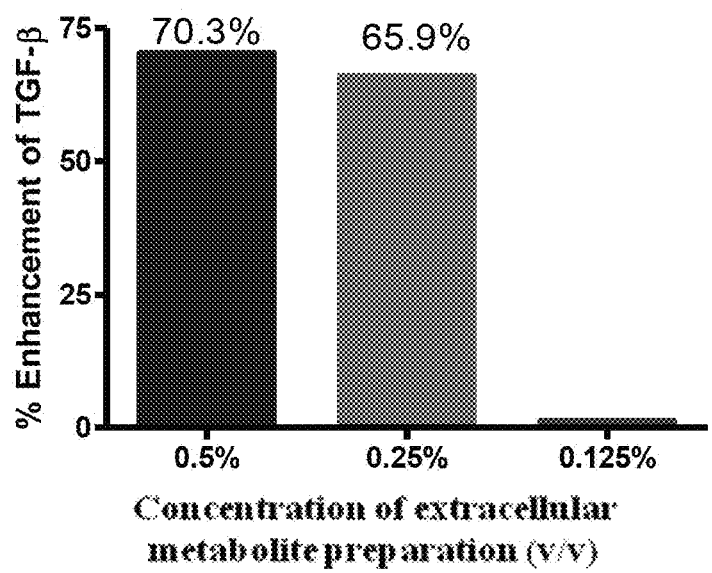
FIG. 2 is the graphical representation of the percentage increase in the expression of TGF-β2 in the dermal papilla cells in the presence of partially purified extracellular metabolite preparation from *Bacillus coagulans* MTCC 5856.
Figure 3:
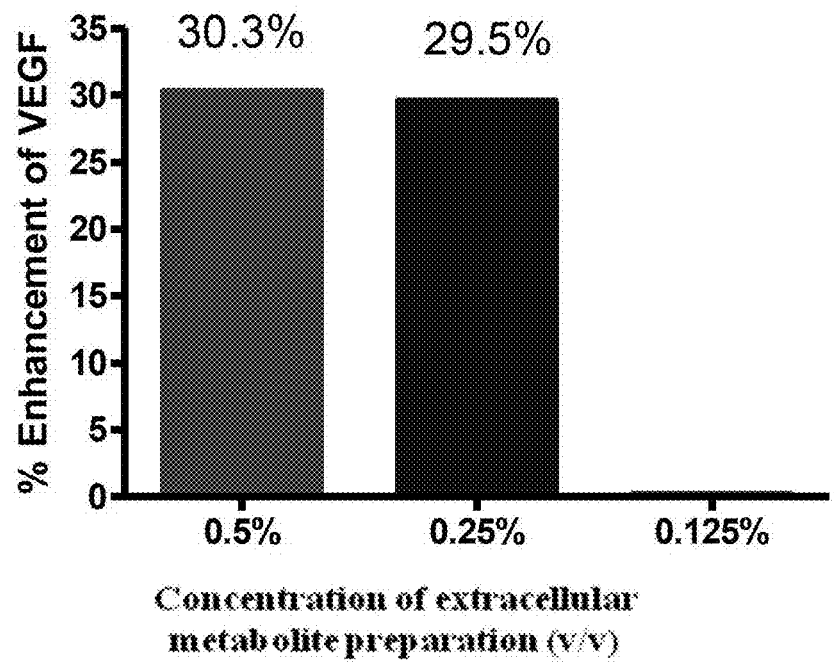
FIG. 3 is the graphical representation of the percentage increase in the expression of VEGF in the dermal papilla cells in the presence of partially purified extracellular metabolite preparation from *Bacillus coagulans* MTCC 5856.

Dermal Papilla Cells were used for the assay at a seeding density of 5000 cells per well of 96-well clear bottom microplate in DMEM and incubated at 37° C. in 95% air and 5% $CO_2$ in a $CO_2$ incubator for 24 hours. Culture supernatants were collected and stored at −80° C. until use. TGF-β and VEGF-1 were detected using ELISA kits (Quantikine® ELISA kit for human TGF-β2 and human VEGF kit, Krishgen biosystems) as per manufacturer's instructions Result The extracellular metabolite increased the expression of TGF-β2 (FIG. 2) by 70.3% at a concentration of 0.5% v/v while a 30% increase in VEGF expression (FIG. 3) was observed, indicating that the extracellular metabolite from *Bacillus coagulans* MTCC 5856 increases the proliferation of dermal papilla and thereby promoting hair growth.

Example 2: 5α-Reductase Inhibition

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus* ferment filtrate extract) from Sabinsa Corporation, USA.

Materials and Method

Figure 4A:
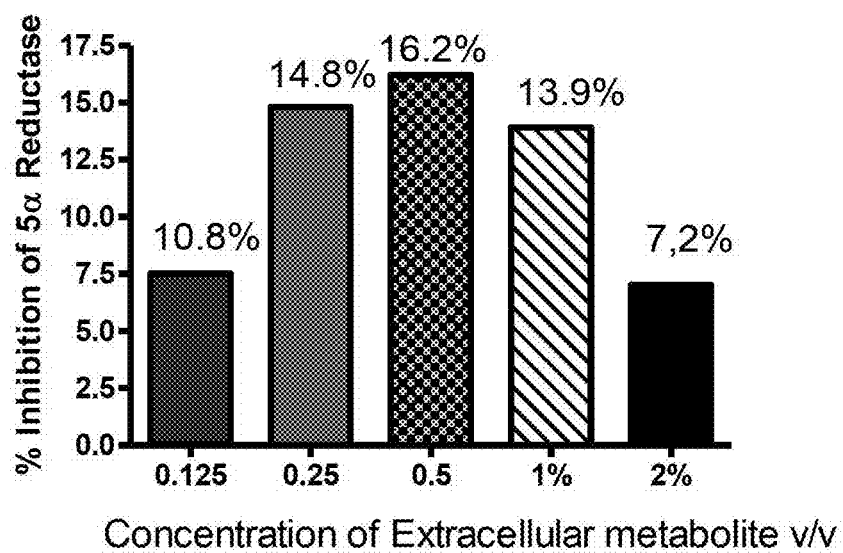
FIG. 4*a* depicts the percentage inhibition of 5α-reductase by partially purified extracellular metabolite preparation from *Bacillus coagulans* MTCC 5856.
Figure 4B:
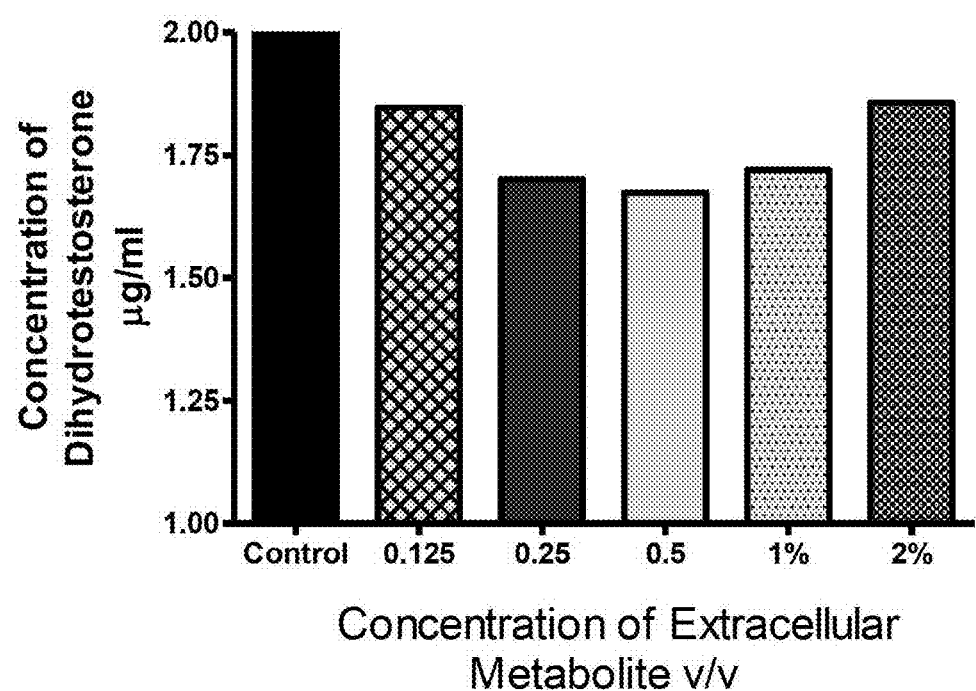
FIG. 4*b* is the graphical representation showing decrease in concentration of dihydrotestosterone due to the inhibition of 5α-reductase activity by partially purified extracellular metabolite preparation from *Bacillus coagulans* MTCC 5856.

Cells: Dermal Papilla Cells (human HFDPC) were purchased from Promocell (Germany), and maintained as a monolayer culture in Fibroblast growth media (Promocell, Germany) at 37° C. in a humidified 5% $CO_2$ incubator. Dermal papilla cells (DPC) were cultured in DMEM medium with 10% FBS and seeded in 96 well tissue culture plate. 24 hrs post seeding, DPC were treated with 50 nM testosterone with & without the test samples and incubated for 48 hrs in a 5% $CO_2$ incubator at 37° C. After 48 hrs the supernatant was collected from each well. The amount of 5α-DHT produced by the various treated DPCs was quantified using ELISA and absorbance was measured at 450 nm using a microplate reader Conclusion The results indicated that the extracellular metabolite preparation brought about 16.2% inhibition in 5α-reductase activity (FIG. 4a), and dihydrotestosterone levels (FIG. 4b) in vitro at 0.5% indicating its potential as a potent 5α-reductase inhibitor for treating clinical conditions like androgenic alopecia.

Example 3: Hair Care Formulations Containing Extracellular Metabolite Preparation from *Bacillus coagulans*

Tables 1—provide illustrative examples of hair care formulations containing partially purified extracellular metabolite preparation from *Bacillus coagulans* MTCC 5856 (*Bacillus* ferment filtrate extract)

TABLE 1

Hair serum

Active Ingredients

Bacillus ferment filtrate extract 0.01%-2%

Excipients

Cationic polymers (Galsilk 700), Disodium EDTA, glycerin, Preservatives, non-ionic surfactant (Tween 20), non-ionic solubilizers and emulsifying agents (Cremophor RH 40), Bioavailability enhancers (Piperine extract or Tetrahydropiperine (Cosmoperine ®)), Fragrance, Thickeners (Cellulose derivatives or Acrylates Cross Polymer)

TABLE 2

Hair serum

Active Ingredients

Bacillus ferment filtrate extract 0.01%-2%
Amla extract, Cocus nucifera
extract, Cosmetic peptides, Selenium sulphide, Vitamin A, C

Excipients

Cationic polymers (Galsilk 700), Disodium EDTA, glycerin, Preservatives, non-ionic surfactant (Tween 20), non-ionic solubilizers and emulsifying agents (Cremophor RH 40), Bioavailability enhancers (Piperine extract or Tetrahydropiperine (Cosmoperine ®)), Fragrance, Thickeners (Cellulose derivatives or Acrylates Cross Polymer)

TABLE 3

Hair oil

Active Ingredients

Bacillus ferment filtrate extract 0.01%-2%
Tea tree oil/coleus oil, Cedarwood oil

Excipients

Flavouring agent, Preservatives, Carrier oils, Bioavailability enhancers (Piperine extract), Selenium containing amino acids, Selenium sulfide, Antioxidants (Vitamins, rosmarinic acid)

TABLE 4

Hair oil

Active Ingredients

Bacillus ferment filtrate extract 0.01%-2%
Almond oil, Amino acids (Methionine, Cysteine), Selenium Sulfide, Vitamins E, A

Excipients

Flavouring agent, Preservatives, Carrier oils, Bioavailability enhancers (Piperine extract, Tetrahydropiperine (Cosmoperine ®)), Antioxidants (rosmarinic acid)

TABLE 5

Anti-dandruff shampoo

Active Ingredients

Bacillus ferment filtrate extract 0.01%-2%
Antifungal agents (ketoconazole), Tea tree oil/Coleus oil, Amino acids (Cysteine, Methionine)

TABLE 5-continued

Anti-dandruff shampoo

Excipients

Selenium sulfide, Cooling agents (Menthol), non-ionic Surfactants (Tween 20), Humectants, Conditioning agents, Preservatives, Antioxidants, Thickeners, Chelating agents or sequestering agents, pH Neutralizer, Detergents The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of increasing hair growth and preventing hair loss in mammals, said method comprising steps of administering effective concentration of extracellular metabolite preparation from Bacillus coagulans MTCC 5856 to said mammals, to bring about increase in hair growth wherein said extracellular metabolite is isolated using a process comprising steps of:
    a) Inoculating a culture of Bacillus coagulans MTCC 5856 into 1.0 liter of Glucose Yeast Extract Acetate broth medium or MRS broth containing 0.5% Tween 80 or Corn steep powder media to initiate bacterial fermentation;
    b) Allowing the bacterial fermentation in the inoculated medium of step a to proceed for 24-48 h at 37° C. with 120 rpm;
    c) Centrifuging the fermentation broth of step b at 4000-7000 rpm and collecting supernatant;
    d) Concentrating supernatants 10 fold by using rotary evaporator at 50° C. of step c;
    e) Adding 150 ml of chilled acetone drop by drop to 100 ml of tenfold concentrated supernatants of step d, followed by mixing to form supernatants-acetone mixture;
    f) Incubating the supernatants-acetone mixture of step e at 0° C. for 30 minutes followed by centrifuging at 7000-8000 rpm to collect a pellet;
    g) Discarding the pellet obtained in step f and collecting 60% (v/v) acetone saturated supernatant (~200 ml);
    h) Concentrating the acetone saturated supernatant in step g to 50 ml by rotary evaporator;
    i) Adjusting the pH of the supernatant of step h to 5.0 by using 4N HCl, filtered (0.22 micron; Millex, Millipore, India) and stored at −20° C. till further use;
    j) Freeze drying the supernatant of step i to obtain partially purified extracellular metabolite preparation from the probiotic bacterial strain Bacillus coagulans MTCC 5856.

2. The method as in claim 1, wherein the increase in hair growth is brought about by a) increasing the expression of TGF-β2 and VEGF in dermal papilla b) increasing the proliferation of follicle dermal papilla cells, and c) inhibiting 5α-reductase activity.

3. The method as in claim 1, wherein the effective concentration of the extracellular metabolite preparation is 0.01% v/v to 2.0% v/v.

* * * * *